US00PP24985P2

(12) United States Plant Patent
Dummen

(10) Patent No.: US PP24,985 P2
(45) Date of Patent: Oct. 21, 2014

(54) ***EUPHORBIA* PLANT NAMED 'DUESTAWHIFLA'**

(50) Latin Name: *Chamaesyce hypericifolia*
Varietal Denomination: Duestawhifla

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 45 days.

(21) Appl. No.: 13/815,027

(22) Filed: Jan. 26, 2013

(51) Int. Cl.
*A01H 5/00* (2006.01)

(52) U.S. Cl.
USPC ..... Plt./302

(58) Field of Classification Search
CPC ..... A01H 1/00; A01H 3/00; A01H 4/00; A01H 5/00
USPC ..... Plt./302
See application file for complete search history.

*Primary Examiner* — Anne Grunberg
(74) *Attorney, Agent, or Firm* — C. A. Whealy

(57) ABSTRACT

A new and distinct cultivar of *Euphorbia* plant named 'Duestawhifla', characterized by its compact, upright, outwardly spreading and mounding plant habit; moderately vigorous growth habit; freely branching habit; and numerous white-colored flowers.

1 Drawing Sheet

Botanical designation: *Chamaesyce hypericifolia.*
Cultivar denomination: 'DUESTAWHIFLA'.

BACKGROUND OF THE INVENTION

The present invention relates to a new and distinct cultivar of *Euphorbia* plant, botanically known as *Chamaesyce hypericifolia* and hereinafter referred to by the name 'Duestawhifla'.

The new *Euphorbia* plant is a product of a planned breeding program conducted by the Inventor in Rheinberg, Germany. The objective of the breeding program is to create new compact *Euphorbia* plants with freely branching and flowering habit.

The new *Euphorbia* plant originated from an open-pollination in July, 2009 in Rheinberg, Germany of a proprietary selection of *Chamaesyce hypericifolia* identified as code number F-02-02, not patented, as the female, or seed, parent with an unknown selection of *Chamaesyce hypericifolia* as the male, or pollen, parent. The new *Euphorbia* plant was discovered and selected by the Inventor as a single flowering plant from within the progeny of the stated open-pollination in a controlled greenhouse environment in Rheinberg, Germany in May, 2011.

Asexual reproduction of the new *Euphorbia* plant by vegetative cuttings in a controlled greenhouse environment in Rheinberg, Germany since July, 2011 has shown that the unique features of this new *Euphorbia* plant are stable and reproduced true to type in successive generations.

SUMMARY OF THE INVENTION

Plants of the new *Euphorbia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duestawhifla'.

These characteristics in combination distinguish 'Duestawhifla' as a new and distinct *Euphorbia* plant:

1. Compact, upright, outwardly spreading and mounding plant habit.
2. Moderately vigorous growth habit.
3. Freely branching habit.
4. Numerous white-colored flowers.

The new *Euphorbia* can be compared to plants of the female parent selection. Plants of the new *Euphorbia* differ primarily from plants of the female parent selection in leaf color as plants of the new *Euphorbia* have lighter green-colored leaves than plants of the female parent selection.

Plants of the new *Euphorbia* can also be compared to plants of *Euphorbia* 'Inneuphdia', disclosed in U.S. Plant Pat. No. 17,567. In side-by-side comparisons, plants of the new *Euphorbia* differed from plants of 'Inneuphdia' in the following characteristics:

1. Plants of the new *Euphorbia* were more compact than plants of 'Inneuphdia'.
2. Plants of the new *Euphorbia* had shorter internodes than plants of 'Inneuphdia'.
3. Plants of the new *Euphorbia* had larger leaves than plants of 'Inneuphdia'.
4. Plants of the new *Euphorbia* had larger flowers than plants of 'Inneuphdia'.

BRIEF DESCRIPTION OF THE PHOTOGRAPH

The accompanying colored photograph illustrates the overall appearance of the new *Euphorbia* showing the colors as true as it is reasonably possible to obtain in colored reproductions of this type. Colors in the photograph may differ slightly from the color values cited in the detailed botanical description which accurately describe the colors of the new *Euphorbia* plant.

The photograph is a side perspective view of a typical flowering plant of 'Duestawhifla' grown in a container.

DETAILED BOTANICAL DESCRIPTION

The aforementioned photograph and following observations, measurements and values describe plants grown during the summer in 12-cm containers in a glass-covered greenhouse in Rheinberg, Germany and under cultural practices typical of commercial *Euphorbia* production. During the production of the plants, day and night temperatures averaged 22° C. and light levels averaged 4,500 lux. Plants were pinched one time three weeks after planting and were 16 weeks old when the photograph and description were taken. In the following description, color references are made to The Royal Horticultural Society Colour Chart, 1995 Edition, except where general terms of ordinary dictionary significance are used.

Botanical classification: *Chamaesyce hypericifolia* 'Duestawhifla'.

Parentage:

*Female, or seed, parent*.—Proprietary selection of *Chamaesyce hypericifolia* identified as code number F-02-02, not patented.

*Male, or pollen, parent*.—Unknown selection of *Chamaesyce hypericifolia*, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; white in color.

*Rooting habit*.—Freely branching; dense.

Plant description:

*Plant form and growth habit*.—Compact, upright, outwardly spreading and mounding plant habit; broad inverted triangle; moderately vigorous growth habit.

*Branching habit*.—Freely branching, usually about three to five primary branches each with numerous secondary and tertiary lateral branches developing per plant.

*Plant height*.—About 12 cm.

*Plant diameter*.—About 30 cm.

*Lateral branch description*.—Length: About 12 cm. Diameter: About 3 mm. Internode length: About 2.4 cm. Strength: Moderately strong. Texture: Smooth, glabrous. Color: Close to 146A.

Foliage description:

*Arrangement*.—Opposite; simple.

*Length*.—About 4.8 cm.

*Width*.—About 1.1 cm.

*Shape*.—Elliptical.

*Apex*.—Acute.

*Base*.—Attenuate to acute.

*Margin*.—Entire.

*Texture, upper surface*.—Pubescent.

*Texture, lower surface*.—Pubescent; rugose.

*Venation*.—Pinnate, arcuate.

*Color*.—Developing leaves, upper surface: Close to 146A. Developing leaves, lower surface: Close to 146B. Fully developed leaves, upper surface: Close to 138A; venation, close to 147A. Fully developed leaves, lower surface: Close to 147B; venation, close to 147C.

*Petioles*.—Length: About 1.2 cm. Diameter: About 1 mm. Texture, upper and lower surfaces: Smooth, glabrous. Color, upper surface: Close to 146A. Color, lower surface: Close to 146B.

Inflorescence description:

*Flower arrangement and flowering habit*.—Single rotate flowers arranged in umbel-like compound terminal cymes; very freely flowering with numerous flower buds and flowers per plant; flowers face upright and outwardly.

*Fragrance*.—None detected.

*Natural flowering season*.—Plants flower naturally during the spring and summer in Germany; flowering continuous during this period; plants begin flowering about eight weeks after planting.

*Flower longevity on the plant*.—About ten days; flowers persistent.

*Flower diameter*.—About 1.3 cm.

*Flower depth* (*height*).—About 1 cm.

*Floral bracts*.—Quantity and arrangement: Two per flower; opposite. Length: About 9 mm. Width: About 2 mm. Shape: Elliptical to lanceolate. Apex: Rounded to acute. Base: Fused. Margin: Entire. Texture, upper and lower surfaces: Smooth, glabrous. Color: When opening and fully opened, upper surface: Close to 155D; color does not change with development. When opening and fully opened, lower surface: Close to 155D; color does not change with development. Bract petioles: Length: About 2 mm. Diameter: About 1 mm. Texture, upper and lower surfaces: Smooth, glabrous. Color, upper and lower surfaces: Close to 146B.

*Peduncles*.—Length: About 2.5 cm. Diameter: About 1 mm. Strength: Strong. Texture: Smooth, glabrous. Color: Close to 146A.

*Cyathia*.—Length: About 4 mm. Diameter: About 3 mm. Shape: Ovate. Aspect: Upright. Texture: Smooth, glabrous. Color, immature and mature: Close to 144A.

*Nectaries*.—Quantity per cyathium: One. Length: About 1 mm. Width: About 1 mm. Shape: Lunate. Texture: Smooth, glabrous. Color, immature and mature: Close to 146A; towards the apices, close to 155D.

*Reproductive organs*.—Androecium: Quantity per cyathium: About four. Filament length: About 2 mm to 3 mm. Filament color: Close to 155D. Anther length: About 0.5 mm. Anther color: Close to 158C. Pollen: Scarce. Pollen color: Close to 158D. Gynoecium: Quantity per cyathium: One. Pistil length: About 3 mm. Style length: About 0.5 mm. Style color: Close to 155D. Stigma shape: Crested. Stigma color: Close to 155D. Ovary color: Close to 144A. Seeds and fruits: Seed and fruit development have not been observed on plants of the new *Euphorbia*.

Temperature tolerance: Plants of the new *Euphorbia* have been observed to tolerate temperatures ranging from about 5° C. to about 40° C.

Pathogen & pest resistance: Plants of the new *Euphorbia* have not been observed to be resistant to pathogens and pests common to *Euphorbia* plants.

It is claimed:

1. A new and distinct *Euphorbia* plant named 'Duestawhifla' as illustrated and described.

* * * * *

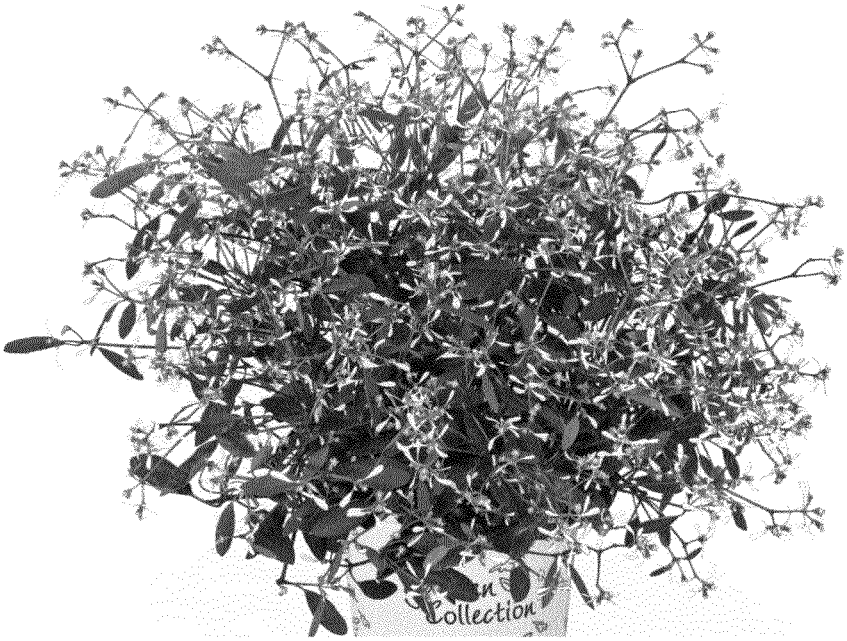
Collection